United States Patent [19]

O'Brien et al.

[11] Patent Number: 5,244,660
[45] Date of Patent: Sep. 14, 1993

[54] USE OF BACILLUS THURINGIENSIS BERLINER VAR. KURSTAKI TO REDUCE THE OCCURRENCE OF DARKLING BEETLES IN POULTRY HOUSES

[76] Inventors: Gerard T. O'Brien; A. Geri O'Brien, both of 2162 Skyline Dr., Gainesville, Ga. 30501

[21] Appl. No.: 828,202

[22] Filed: Jan. 30, 1992

[51] Int. Cl.$^5$ ............................................. A01N 63/00
[52] U.S. Cl. .................................................. 424/93 L
[58] Field of Search ...................................... 424/93 L

[56] References Cited

U.S. PATENT DOCUMENTS 4,764,372  8/1988  Herrnstadt et al. .............. 424/93 L
5,064,648  11/1991 Hickle et al. ..................... 424/93 L Primary Examiner—Douglas W. Robinson
Assistant Examiner—Jean C. Witz

[57] ABSTRACT

The application of *Bacillus thuringiensis* berliner var. Kurstaki to poultry houses results in the reduction of the larger and smaller darkling beetle infesting those houses.

1 Claim, No Drawings

USE OF *BACILLUS THURINGIENSIS* BERLINER VAR. KURSTAKI TO REDUCE THE OCCURRENCE OF DARKLING BEETLES IN POULTRY HOUSES

BACKGROUND OF THE INVENTION

1. Field of the Invention

The darkling beetle, [Alphitobius diapermis] tends to infest poultry houses and is an expensive nuisance because they tend to damage wood structures, insulation, and sometimes electrical wiring insulation. Some reports have mentioned that the beetle also harbours the salmonella bacteria and thus can infect the poultry flock residing in the poultry building—because the fowl eat the beetles.

[Bacillus thuringiencis] is known as a bacteria that will be taken up by various insects and their larvae and then the bacteria kills off these hosts. It has been used on the silk worm and flour moth with good success.

The invention teaches that the B.t. will be taken up by the darkling beetle and thus these beetles will be eradicated because they die after absorbing the B.t.

Lab experiments have shown that the large darkling beetle, E, Tenebrio is killed off by the B.t.; and thus by extension the small darkling beetles [Alphitobius diapermis], that infest the poultry houses, will also be killed off by the B.t. after they are exposed to it and take it up. Indeed lab experiments have shown that the B.t. is truly effective against both beetles. It is effective because it kills off the larvae of both types of beetles.

2. Description of Prior Art

The open poultry industry literature periodically reports a general dissatisfaction within the industry with control and eradication methods regarding the darkling beetle in poultry housing. It would appear that at the present time there is no satisfactory way to "kill off" or control the darkling beetle population in the poultry housing.

Some people clean out the poultry houses periodically, removing litter and poultry manure, and then spray the inside of each house with disinfectant to kill off any bacteria and darkling beetles that might still be left in the empty house.

One farm we visited a few months ago had sprayed with cresol which contains about 2% phenol; and this indeed appeared to have eradicated the darkling beetle population—since none could be found in those poultry houses. But, on the other hand, many of the fowl then populating those houses appeared stricken with various ailments that could possibly be attributed to the residual cresol/phenol. Maladies such as: semicomatose state, loss of walking ability, and so on.

Cresol/phenol is also hostile to people, and precautions have to be taken when applying the spray to the housing interiors so that the people involved do not "take up" any of the chemical mixture. It may not be possible to guarantee zero "take up" by the farm personnel, either during spraying, or later off the building surfaces, and indeed via litter dust that may have "taken up" the residual cresol/phenol.

B.t. on the other hand is generally conceded to be relatively safe for humans to handle and may be bought easily in most cities for even non-farm uses—such as gardening. So its application to poultry houses for eradication of the darkling beetle appears to present no safety/handling problems, should be relatively benign to poultry at all stages of development, and will allow healthier and thus higher quality poultry meat to be raised for the dinner table. May even lower the salmonella bacterial loading on the poultry because it kills off the salmonella carrying darkling beetles which the poultry would otherwise be ingesting. May even lower the 'poultry tape worm' loading on the poultry because it kills off the tape worm carrying darkling beetles which the poultry would otherwise be ingesting.

SUMMARY OF THE INVENTION

Application of [Bacillus thuringiensis] to darkling beetles [Alphitobius diapermis and tenebrid] in poultry houses and other places will ensure effective eradication and therefore control of their population where they are not desired.

B.t. is reasonably safe for humans and most animals and fowl when used according to the manufacturers instructions. It would appear to be much safer than present conventional: insecticides, pesticides and fumigants presently being used for control of the darkling beetle in poultry houses.

DESCRIPTION OF THE PREFERRED EMBODIMENT

The B.t. will be applied to the empty, cleaned, poultry houses prior to putting in the litter and poultry.

The B.t. could be applied by hand broadcasting, dusting, spraying, or fogging, whichever is most approved by the B.t. manufacturer and/or supplier.

All EDA, USDA, EPA, and other local regulations (if any) must be strictly adhered to.

The B.t. could of course be also applied to the top of the litter on the floor prior to putting the fowl into the housing and indeed periodically thereafter as needed—in case fresh infestation of darling beetles were introduced after the earlier applications.

There is a possibility that the B.t., being a bacteria, will thrive and grow in the poultry house litter since all of the nutrients and moisture needed for its viability are usually present in the poultry house litter. This being so, one or two applications to the original litter may be all that is needed.

We claim:

1. A method to reduce the occurrence of the larger darkling beetle and the smaller darkling beetle in poultry houses consisting of applying an effective amount of *Bacillus thuringiensis* berliner var kurstaki to said beetles or their larvae infesting said poultry house.

* * * * *